(12) United States Patent
Voskuhl

(10) Patent No.: US 10,799,512 B2
(45) Date of Patent: Oct. 13, 2020

(54) ESTROGEN COMBINATION FOR TREATMENT OF MULTIPLE SCLEROSIS

(71) Applicant: The Regents of the University of California, Oakland, CA (US)

(72) Inventor: Rhonda R. Voskuhl, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/307,180

(22) PCT Filed: Apr. 27, 2015

(86) PCT No.: PCT/US2015/027752
§ 371 (c)(1),
(2) Date: Oct. 27, 2016

(87) PCT Pub. No.: WO2015/168000
PCT Pub. Date: Nov. 5, 2015

(65) Prior Publication Data
US 2017/0049785 A1    Feb. 23, 2017

Related U.S. Application Data

(60) Provisional application No. 62/032,952, filed on Aug. 4, 2014, provisional application No. 61/985,184, filed on Apr. 28, 2014, provisional application No. 61/985,380, filed on Apr. 28, 2014, provisional application No. 62/050,918, filed on Sep. 16, 2014.

(51) Int. Cl.

| A61K 31/566 | (2006.01) |
| A61K 31/57 | (2006.01) |
| A61K 45/06 | (2006.01) |
| A61K 31/567 | (2006.01) |
| A61K 31/565 | (2006.01) |
| A61K 38/13 | (2006.01) |
| A61K 38/21 | (2006.01) |

(52) U.S. Cl.
CPC .......... *A61K 31/566* (2013.01); *A61K 31/565* (2013.01); *A61K 31/567* (2013.01); *A61K 31/57* (2013.01); *A61K 38/13* (2013.01); *A61K 38/215* (2013.01); *A61K 45/06* (2013.01)

(58) Field of Classification Search
CPC ............................ A61K 31/566; A61K 31/565
USPC ......................................................... 514/170
See application file for complete search history.

(56) References Cited

U.S. PATENT DOCUMENTS

| 3,932,635 | A | 1/1976 | Segre |
| 4,826,831 | A | 5/1989 | Plunkett et al. |
| 5,108,995 | A | 4/1992 | Casper |
| 6,936,599 | B2 | 8/2005 | Voskuhl |
| 8,372,826 | B2 | 2/2013 | Voskuhl |
| 8,658,627 | B2 | 2/2014 | Voskuhl |
| 8,895,539 | B2 | 11/2014 | Voskuhl |
| 9,168,262 | B2 | 10/2015 | Voskuhl |
| 9,452,175 | B2 | 9/2016 | Voskuhl |
| 9,962,395 | B2 | 5/2018 | Voskuhl |
| 10,369,158 | B2 | 8/2019 | Voskuhl |
| 10,406,169 | B2 | 9/2019 | Voskuhl |
| 2005/0113350 | A1 | 5/2005 | Duesterberg et al. |
| 2005/0239758 | A1 | 10/2005 | Roby |
| 2009/0005351 | A1 | 1/2009 | Pickar et al. |
| 2010/0168071 | A1 | 7/2010 | Boissonneault |
| 2010/0203016 | A1 | 8/2010 | Voskuhl |
| 2012/0282222 | A9 | 11/2012 | Voskuhl et al. |
| 2013/0203722 | A1 | 8/2013 | Voskuhl |
| 2017/0049785 | A1 | 2/2017 | Voskuhl |
| 2017/0290845 | A1 | 10/2017 | Voskuhl |

FOREIGN PATENT DOCUMENTS

| AU | 2004257772 A1 | 1/2005 |
| WO | WO-01070208 A2 | 9/2001 |
| WO | WO-2002/085364 A1 | 10/2002 |
| WO | WO-2002/085374 | 10/2002 |
| WO | WO-2002/092102 A2 | 11/2002 |
| WO | WO-2002/092102 A3 | 11/2002 |
| WO | WO-2007/038435 A2 | 4/2007 |
| WO | WO-2007/038636 A2 | 4/2007 |
| WO | WO-2008/150547 A1 | 12/2008 |
| WO | WO2008150547 | * 12/2008 |
| WO | WO-2010/050916 A1 | 5/2010 |
| WO | WO-2015/168000 A1 | 11/2015 |

OTHER PUBLICATIONS

Gold et al. Journal of the Neurological Sciences, vol. 286 (2009), pp. 99-103.*
Rosti et al. Multiple Sclerosis (2006), vol. 12, pp. 586-593 (Year: 2006).*
Kieseier et al. (MSJ (2012) vol. 18, pp. 914-924) (Year: 2012).*
Gold et al., "Estrogen treatment in multiple sclerosis," J Neurol Sci, 286(1-2):99-103 (2009).
International Search Report of the International Searching Authority, dated Aug. 3, 2015, from related International Application No. PCT/US2015/027756.
International Search Report of the International Searching Authority, dated Aug. 5, 2015, from related International Application No. PCT/US2015/027752.
International Search Report of the International Searching Authority, dated Jan. 10, 2016, from related International Application No. PCT/US2015/047906.
International Search Report of the International Searching Authority, dated Dec. 24, 2015, from related International Application No. PCT/US2015/052805.

(Continued)

*Primary Examiner* — Taina D Matos Negron
(74) *Attorney, Agent, or Firm* — Foley Hoag LLP; David P. Halstead; Alexander J. Chatterley

(57) ABSTRACT

Provided are methods for treating multiple sclerosis using a continuous regimen of estrogen in combination with periodic administration of a progestogen.

12 Claims, 6 Drawing Sheets

(56) References Cited

OTHER PUBLICATIONS

International Search Report of the International Searching Authority, dated Feb. 16, 2016, from related International Application No. PCT/US2015/056649.
International Search Report of the International Searching Authority, dated Jul. 11, 2016, from related International Application No. PCT/US2016/024754.
International Search Report of the International Searching Authority, dated Jul. 21, 2016, from related International Application No. PCT/US2016/024751.
MacKenzie-Graham et al., "Estrogen treatment prevents gray matter atrophy in experimental autoimmune encephalomyelitis," J Neurosci Res, 90(7):1310-23 (2012).
Prempro and Premphase drug information, Food and Drug Administration, dated Jun. 5, 2003, Retrieved from the Internet. URL: http://www.fda.gov/ohrms/dockets/ac/03/briefing/3992B1_03_FDA-Prempro-Premphase.pdf.
Smith et al., "Impact of combined estradiol and norethindrone therapy on visuospatial working memory assessed by functional magnetic resonance imaging," J Clin Endocrinol Metab, 91(11):4476-81 (2006).
Speroff et al., "Postmenopausal hormone therapy," Gynecololgy and Obstetrics, Chapter 110, Mar. 8, 2011. URL: http://www.glowm.com/resources/glowm/cd/pages/v1/v1c110.html.
Alhola et al., "Estrogen+ progestin therapy and cognition: A randomized placebo☐controlled double☐blind study," J Obstet Gynaecol Re, 36(4): 796-802 (2010).
Anderer et al., "Age-related cognitive decline in the menopause: effects of hormone replacement therapy on cognitive event-related potentials," Maturitas, 51(3): 254-269 (2005).
Luchetti et al., "Gender Differences in Multiple Sclerosis: Induction of Estrogen Signaling in Male and Progesterone Signaling in Female Lesions," J Neuropathol Exp Neurol, 73(2): 123-135 (2014).
Nicot, "Gender and sex hormones in multiple sclerosis pathology and therapy," Front Biosci (Landmark Ed), 14: 4477-4515 (2009).
Sicotte et al., "Treatment of Multiple Sclerosis with the Pregnancy Hormone Estriol," Ann Neurol, 52(4): 421-428 (2002).
Anderson, "Adding estriol reduces ms relapse rate," Medscape Medical News, pp. 1-4 (2014). [https://www.medscape.com/viewarticle/824364].
Anonymous: "Estriol Treatment in Multiple Sclerosis (MS): Effect on Cognition," ClinicalTrials.gov archive, pp. 1-5 (2013). NCT01466114.
Extended European Search Report issued by the European Patent Office in corresponding Application No. EP 15786314.3, dated Dec. 1, 2017.
Extended European Search Report issued by the European Patent Office in corresponding Application No. EP 15786637.7, dated Dec. 1, 2017.
Kipp et al., "Multiple sclerosis: neuroprotective alliance of estrogen-progesterone and gender," Front Neuroendocrin, 33(1):1-16 (2012).
Soldan et al., "Immune modulation in multiple sclerosis patients treated with the pregnancy hormone estriol," J Immunol, 171(11):6267-6274 (2003).
Luine, "Estradiol and cognitive function: past, present and future," Horm Behav, 66(4):602-618 (2014).
Extended European Search Report issued by the European Patent Office in corresponding Application No. 15846358.8, dated Apr. 17, 2018.
Itoh et al., "Bedside to bench to bedside research: Estrogen receptor beta ligand as a candidate neuroprotective treatment for multiple sclerosis," J Neuroimmunol, 304:63-71 (2017).
Voskuhl et al., "Estriol combined with glatiramer acetate for women with relapsing-remitting multiple sclerosis: a randomised, placebo-controlled, phase 2 trial," Lancet Neurol, 15(1):35-46 (2016).

Spence et al., "Neuroprotective effects of estrogens and androgens in CNS inflammation and neurodegeneration," Front Neuroendocrinol, 33(1):105-115 (2012).
Zhang et al., "Distribution and differences of estrogen receptor beta immunoreactivity in the brain of adult male and female rats," Brain Res, 935(1-2):73-80 (2002).
Rubin, "Parkinson's Disease in Women," American Parkinson Disease Association, https://www.apdaparkinson.org/parkinsons-disease-in-women/ (2015).
Blasco et al., "Amyotrophic Lateral Sclerosis," Informa Healthcare, 13:585-588 (2012).
Chen et al., "The Treatment Strategies for Neurodegenerative Diseases by Integrative Medicine," Integrative Medicine International, 1:223-225 (2014).
Cubo et al., "Effect of Donepezil on Motor and Cognitive Function in Huntington Disease," Neurology, 67(7):1268-1271 (2006).
Aygestin® Label, norethindrone acetate rablets, USP, Rx Only.
Bendfeldt et al., "Effect of immunomodulatory medication on regional gray matter loss in relapsing-remitting multiple sclerosis—A longitudinal MRI study," Brain Research, 1325:174-182 (2010).
Extended European Search Report issued by the European Patent Office in corresponding Application No. PCT/US2016/024754 dated Nov. 21, 2018.
Geurts et al., "Measurement and clinical effect of grey matter pathology in multiple sclerosis," Lancet Neurol, 11:1082-1092 (2012).
Holtorf et al., "The Bioidentical Hormone Debate: Are Bioidentical Hormones (Estradiol, Estriol, and Progesterone) Safer or More Efficacious than Commonly Used Synthetic Versions in Hormone Replacement Therapy?," Postgraduate Medicine, 121(1): 73-85 (2009).
Honjo et al., "Progestins and estrogens and Alzheimer's disease," Journal of Steroid Biochemistry & Molecular Biology, 93:305-308 (2005).
Lanka et al., "Therapy development for ALS: Lessons learned and path forward," Amyotrophic Lateral Sclerosis, 9:131-140 (2008).
MacKenzie-Graham et al., "Estriol-mediated neuroprotection in multiple sclerosis localized by voxel-based morphometry." Brain and behavior: e01086 (2010).
Mayo Clinic, "Huntington's Disease," https:mayoclinic.org/diseases-conditions/huntingtons-disease/symptoms-causes/syc-20356117?p=1 (2008).
Prometrium® Label, progesterone, USP.
Ransohoff et al., "Animal models of multiple sclerosis: the good, the bad and the bottom line," Nature Neuroscience, 15:1074-1077 (2012).
Reed et al., "The Normal Menstrual Cycle and the Control of Ovulation," Europepmc.ord, 1-26 (2018).
Schiff et al., "Effect of Estriol Administration on the Hypogonadal Woman," Fertility and Sterility, 30(3):278-282 (1978).
Schiff et al., "Plasma estriol and its conjugates following oral and vaginal administration of estriol to postmenopausal women: Correlations with gonadotropin levels," Am J Obstet Gynecol, 138(8):1137-1141 (1980).
Sicotte et al., "Treatment of Multiple Sclerosis with Pregnancy Hormone Estriol," Ann Neurol, 52:421-428 (2002).
Tiwari-Woodruff et al., "Neuroprotective and anti-inflammatory effects of estrogen receptor ligand treatment in mice," Journal of Neurological Sciences, 286:81-85 (2009).
Tolppanen et al., "Systemic Estrogen Use and Discontinuation After Alzheimer's disease Diagnosis in Finland 2005-2012: A Nationwide Exposure-Matched Cohort Study," Drugs & Aging, 35:985-992 (2018).
Vickers, "A Vaccine Against Alzheimer's Disease," Drugs Aging, 19:487-494 (2002).
Zivadinov et al., "Interferon beta-1a slows progression of atrophy in relapsing-remitting multiple sclerosis predominantly by reducing gray matter atrophy," Multiple Sclerosis, 13:490-501 (2007).

* cited by examiner

ESTROGEN COMBINATION FOR TREATMENT OF MULTIPLE SCLEROSIS

PRIORITY CLAIM

This application is a § 371 national-stage application based on PCT Application PCT/US2015/027752, filed Apr. 27, 2015 which claims priority to U.S. Provisional Patent Application No. 61/985,184, filed on Apr. 28, 2014, U.S. Provisional Patent Application No. 61/985,380, filed on Apr. 28, 2014, U.S. Provisional Patent Application No. 62/032,952, filed on Aug. 4, 2014, and U.S. Provisional Patent Application No. 62/050,918, filed on Sep. 16, 2014, each of which is hereby incorporated by reference in its entirety.

GOVERNMENT SUPPORT

This invention was made with government support under Grant Number NS051591, awarded by the National Institutes of Health. The government has certain rights in the invention.

BACKGROUND

Multiple sclerosis (MS) is a chronic, often debilitating disease affecting the central nervous system (brain and spinal cord). MS affects more than 1 million people worldwide and is the most common neurological disease among young adults, particularly women. The exact cause of MS is still unknown. MS is an autoimmune disease in which myelin sheaths surrounding neuronal axons are destroyed. This condition can cause weakness, impaired vision, loss of balance, and poor muscle coordination.

MS takes several forms, with new symptoms either occurring in isolated attacks (relapsing forms) or building up over time (progressive forms). Between attacks, symptoms may disappear completely; however, permanent neurological problems often occur, especially as the disease advances.

In 1996, the United States National Multiple Sclerosis Society described four clinical subtypes of MS: (i) relapsing-remitting; (ii) secondary-progressive; (iii) primary-progressive; and (iv) progressive-relapsing.

Relapsing-remitting MS is characterized by unpredictable relapses followed by periods of months to years of relative quiet (remission) with no new signs of disease activity. Deficits that occur during attacks may either resolve or leave sequelae, the latter in about 40% of attacks and being more common the longer a person has had the disease. This describes the initial course of 80% of individuals with MS. When deficits always resolve between attacks, this is sometimes referred to as benign MS, although people will still build up some degree of disability in the long term. On the other hand, the term malignant multiple sclerosis is used to describe people with MS having reached significant level of disability in a short period of time. The relapsing-remitting subtype usually begins with a clinically isolated syndrome (CIS). In CIS, a person has an attack suggestive of demyelination but does not fulfill the criteria for multiple sclerosis; 30 to 70% of persons experiencing CIS go on to develop MS.

Secondary-progressive MS occurs in around 65% of those with initial relapsing-remitting MS, who eventually have progressive neurologic decline between acute attacks without any definite periods of remission. Occasional relapses and minor remissions may appear. The median length of time between disease onset and conversion from relapsing-remitting to secondary progressive MS is 19 years.

Primary-progressive MS occurs in approximately 0-20% of individuals, with no remission after the initial symptoms. It is characterized by progression of disability from onset, with no, or only occasional and minor, remissions and improvements. The usual age of onset for the primary progressive subtype is later than of the relapsing-remitting subtype, but similar to the age that secondary-progressive MS usually begins in relapsing-remitting MS, around 40 years of age.

Progressive-relapsing MS describes those individuals who, from onset, have a steady neurologic decline but also have clear superimposed attacks. This is the least common of all subtypes.

Currently the following agents are approved by the U.S. Food and Drug Administration (FDA) to reduce disease activity and disease progression for many people with relapsing forms of MS, including relapsing-remitting MS, as well as secondary-progressive and progressive-relapsing MS in those people who continue to have relapses: dimethyl fumarate (Tecfidera®, BG-12), fingolimod (Gilenya®), glatiramer acetate (Copaxone®), interferon beta-1a (Avonex® and Rebif®), interferon beta-1b (Betaseron® and Extavia®), mitoxantrone (Novantrone®), natalizumab (Tysabri®), and teriflunomide (Aubagio®). However, many of these therapies fail to successfully treat all patients or all symptoms in treated patients, and many of these therapies are associated with undesirable side effects. Accordingly, alternative therapies are needed.

SUMMARY

An aspect of the invention is a method of treating multiple sclerosis, comprising administering to a subject in need thereof, on a continuous basis throughout one or more (preferably at least two) consecutive treatment periods, a therapeutically effective amount of an estrogen; and administering to the subject, for only a portion of each treatment period, a therapeutically effective amount of a progestogen.

In certain embodiments, the estrogen is selected from estriol (E3), estradiol (E2), estrone (E1), pharmaceutically acceptable salts of any of the foregoing, and any combination thereof.

In certain embodiments, the estrogen is estriol.

In certain embodiments the progestogen is selected from chlormadinone acetate, cyproterone acetate, desogestrel, dienogest, 5α-dihydroprogesterone, drospirenone (Yasmit®), ethanediol acetate, ethynodiol diacetate, etonouestrel (Nexplanon®), gestodene, 17-hydroxyprogesterone, levonorgestrel (Alesse®), medroxyprogesterone acetate (17α-hydroxy-6α-methylprogesterone acetate; Provera®), megestrol, megestrol acetate (17αacetoxy-6-dehydro-6-methylprogesterone), nestorone, nomegestrol acetate, norethindrone, norethindrone acetate (also known as norethindrone acetate), norethynodrel Enovid®), norgestimate, norgestrel, progesterone, tanaproget, trimegestone, pharmaceutically acceptable salts of any of the foreoing, and any combination thereof.

In certain embodiments, the progestogen is progesterone.

In certain embodiments, the progestogen is norethindrone.

In certain embodiments, the estrogen is administered orally in a dose equal or equivalent to about 8 mg of estriol daily.

In certain embodiments, the progestogen is administered orally in a dose equal or equivalent to about 700 μg of norethindrone daily.

An aspect of the invention is a method of treating multiple sclerosis, comprising administering orally to a subject in need thereof, on a continuous basis for 84 consecutive days (12 weeks), 8 mg of estriol daily; and administering orally to the subject, for 14 consecutive days (2 weeks) of the 84 consecutive days (12 weeks), 0.7 mg of norethindrone daily.

In certain embodiments, the method further comprises administering to the subject a placebo in place of the norethindrone on each of the days the norethindrone is not administered to the subject.

In certain embodiments, the multiple sclerosis is relapsing-remitting multiple sclerosis.

In certain embodiments, the multiple sclerosis is secondary-progressive multiple sclerosis.

In certain embodiments, the multiple sclerosis is primary-progressive multiple sclerosis.

In certain embodiments, the multiple sclerosis is progressive-relapsing multiple sclerosis.

In certain embodiments, the multiple sclerosis is clinically isolated syndrome (CIS).

In certain embodiments, the method further comprises administering to the subject an immunotherapeutic agent, wherein the immunotherapeutic agent is neither an estrogen nor a progestogen, e.g., an immunotherapeutic agent selected from interferon-beta 1a, interferon-beta 1b, glatiramer acetate, natalizumab mitoxantrone, fingolimod, teriflunomide, and dimethyl fumarate.

In certain embodiments, the subject is a subject being treated with an immunotherapeutic agent yet experiencing a relapse and/or progression of the multiple sclerosis.

Although the methods disclosed throughout the specification and claims are useful for treating multiple sclerosis in its various forms and stages, these methods can also be applied the treatment of other neurodegenerative diseases, such as, by way of illustration, Alzheimer's disease, Parkinson's disease, stroke, amyotrophic lateral sclerosis, cerebellar ataxia, frontotemporal dementia, prion disease, Huntington's Disease, cerebral ischemia, idiopathic Morbus Parkinson, Parkinson syndrome, Morbus Alzheimers, cerebral dementia syndrome, infection-induced neurodegeneration disorders (e.g., AIDS-encephalopathy, Creutzfeld-Jakob disease, encephalopathies induced by rubiola and herpes viruses and borrelioses), metabolic-toxic neurodegenerative disorders (such as hepatic-, alcoholic-, hypoxic-, hypo- or hyperglycemically-induced encephalopathies), encephalopathies induced by solvents or pharmaceuticals, degenerative retina disorders, trauma-induced brain damage, trauma-induced bone marrow damage, cerebral hyperexcitability symptoms, cerebral hyperexcitability states (e.g., of varying origin, such as after the addition of and/or withdrawal of medicaments, toxins, noxae and drugs), neurodegenerative syndromes of the peripheral nervous system, peripheral nerve injury, and spinal cord injury. In certain preferred embodiments, the neurodegenerative disease is multiple sclerosis. In preferred embodiments, the patient is a woman. In some embodiments, the patient is a premenopausal or perimenopausal woman. In other embodiments, the patient is a postmenopausal woman.

In certain embodiments, the method is a method for slowing, halting, or reversing progression of a cognitive or physical disability in a subject with a neurodegenerative disease, comprising identifying a subject who has experienced progression of a cognitive or physical disability and initiating treatment of the subject by a method as described herein. In certain embodiment, the method further comprises testing the severity of the subject's cognitive or physical disability to determine a score representative of the state of the subject's cognitive or physical disability after receiving the treatment for at least about six months, and, optionally, comparing the score to a score determined for the subject prior to or at about the time of initiating the treatment.

Another aspect of the invention relates to a method of terminating estrogen therapy in a subject receiving both estrogen therapy and another immunotherapeutic for the treatment of a neurodegenerative disease, such as multiple sclerosis, wherein the estrogen therapy comprises administering an original dose of estrogen on a regular basis (e.g., daily), by administering to the subject about half of the original dose of the estrogen on the regular basis for a first period of 1-3 weeks (preferably about 2 weeks), then administering to the subject, for a second period of 1-3 weeks (preferably about 2 weeks), about one quarter of the original dose of the estrogen; and after the second period, terminating administration of the estrogen to the patient. In certain such embodiments, the estrogen therapy further comprises administering a progestogen on an intermittent basis, and the method further comprises terminating administration of the progestogen to the patient before the first period or during the first period, preferably before the first period. The estrogen and progestogen can be any estrogen or progestogen described herein, and the original dose can be any suitable therapeutic dose described herein. Administering half or one quarter of the original dose may be accomplished by changing the frequency of administration, the amount of the estrogen administered, or both.

In other aspects, the invention relates to compounds for use in treating neurodegenerative diseases according to any of the various methods disclosed herein, use of compounds in the manufacture of medicaments for carrying out any of the various methods disclosed herein, and kits comprising compounds together with instructions for administering the compounds according to any of the various methods disclosed herein.

DETAILED DESCRIPTION

Figure 1:
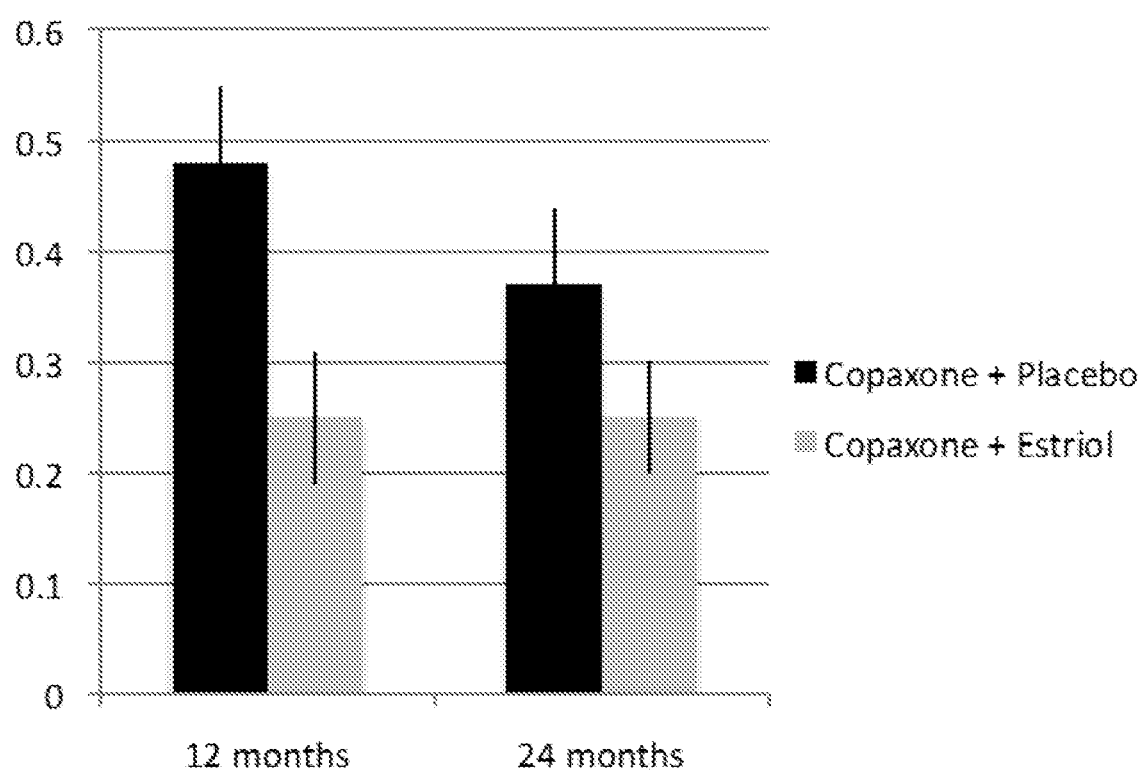
FIG. 1 is a bar graph depicting annualized relapse rates with Copaxone® plus estriol treatment as compared to Copaxone® plus estriol placebo treatment.

Approximately 50% of people diagnosed with multiple sclerosis (MS) will develop problems with cognition. Currently, there are no FDA-approved treatments targeting cognitive function in MS. Multiple sclerosis relapses are known to be significantly decreased by approximately 80% during late pregnancy. This disease improvement may be due to estriol, an estrogen unique to pregnancy. Estriol blood levels go from undetectable levels prior to pregnancy, increase during pregnancy and reach highest levels during late pregnancy. Further, estrogen treatment has been shown to have favorable effects on cognition in animal models of other neurological diseases.

An aspect of the invention is a method of treating multiple sclerosis. The method includes the steps of administering to a subject in need thereof, on a continuous basis throughout two or more consecutive treatment periods, a therapeutically effective amount of an estrogen; and administering to the subject, for only a portion of each treatment period, a therapeutically effective amount of a progestogen.

The term "estrogen" as used herein refers to any biologically active form of estrogen or precursor thereof. The term "estrogen" thus embraces naturally occurring, synthetic, and semi-synthetic forms of estrogen, and biologically active, pharmaceutically acceptable salts and esters thereof. In certain embodiments, estrogen is selected from estriol (E3), estradiol (E2), estrone (E1), an ester thereof, a pharmaceutically acceptable salt of an ester thereof, and any combination of the foregoing. In certain embodiments, estrogen is estriol (E3) or an ester thereof, or a pharmaceutically acceptable salt of an ester thereof. For example, the estrogen can be estriol, estriol succinate, estriol dihexanoate, or estriol sulfate. In other embodiments, estrogen is estradiol (E2) or an ester thereof, or a pharmaceutically acceptable salt of an ester thereof, while in yet other embodiments, estrogen is estrone (E1) or an ester thereof, or a pharmaceutically acceptable salt of an ester thereof. In certain preferred embodiments, estrogen is estriol (E3). In certain embodiments, estrogen is estradiol (E2). In certain embodiments, estrogen is estrone (E1).

In certain embodiments, the estrogen is administered in a dose equal or equivalent to about 200 µg to about 20 mg estriol daily. For example, a dose of 2 to 4 mg of estriol is generally considered to be equivalent to 0.6 to 1.25 mg of conjugated estrogens or estrone. In certain embodiments, the estrogen is administered in a dose equal or equivalent to about 1 mg to about 10 mg estriol daily, preferably equal or equivalent to about 8 mg estriol daily. In most preferred embodiments, the estrogen is estriol administered in a dose of about 8 mg estriol daily.

In certain embodiments, the estrogen is formulated for oral administration, e.g., in a dose equal or equivalent to about 200 µg to about 20 mg estriol daily. For example, a dose of 2 to 4 mg of estriol is generally considered to be equivalent to 0.6 to 1.25 mg of conjugated estrogens or estrone. In certain embodiments, the estrogen is formulated for oral administration in a dose equal or equivalent to about 1 mg to about 10 mg estriol daily, preferably equal or equivalent to about 8 mg estriol daily. In most preferred embodiments, the estrogen is estriol formulated for oral administration in a dose of about 8 mg estriol daily.

In certain embodiments, the estrogen is orally administered in a dose equal or equivalent to about 200 µg to about 20 mg estriol daily. For example, a dose of 2 to 4 mg of estriol is generally considered to be equivalent to 0.6 to 1.25 mg of conjugated estrogens or estrone. In certain embodiments, the estrogen is orally administered in a dose equal or equivalent to about 1 mg to about 10 mg estriol daily, preferably equal or equivalent to about 8 mg estriol daily. In most preferred embodiments, the estrogen is estriol orally administered in a dose of about 8 mg estriol daily.

An "effective amount", as used herein, refers to an amount that is sufficient to achieve a desired biological effect. A "therapeutically effective amount", as used herein refers to an amount that is sufficient to achieve a desired therapeutic effect. For example, a therapeutically effective amount can refer to an amount that is sufficient to improve at least one sign or symptom of MS.

A therapeutically effective dose of the estrogen is, in some embodiments, one sufficient to raise the serum concentration above basal levels, and preferably to pregnancy levels or above pregnancy levels. In certain embodiments, the therapeutically effective dose of the estrogen is selected to result in serum levels in a patient equivalent to the steroid hormone level of that agent in women in the second or third trimester of pregnancy.

For example, during the normal female menstrual cycle estradiol levels are in the range of about 350 pg/ml serum. During pregnancy, there is about a 100-fold increase in the level of estradiol to about 10,000 to about 35,000 pg/ml serum. Correale et al. *J Immunol* 161:3365-74 (1998) and Gilmore et al., *J Immunol* 158:446-51 (1997). In contrast, estriol levels are undetectable during the menstrual cycle in the non-pregnant state. Estradiol levels rise progressively during pregnancy to levels from 3,000 to 30,000 pg/ml (3 to 30 ng/ml).

In one embodiment, where the estrogen is estriol, the dose is from about 4 to 16 milligrams daily, and more specifically, about 8 milligrams daily. In this embodiment, blood serum levels preferably reach at least about 2 ng/ml, may reach about 10 to about 35 ng/ml, or most preferably about 20-30 ng/ml. Sicotte et al. *Neurology* 56:A75 (2001). In some embodiments, estradiol (E2) levels would preferably reach at least about 2 ng/ml and most preferably about to 10-35 ng/ml. In some embodiments, estrone (E1) levels would preferably reach at least about 2 ng/ml and most preferably about 5-18 ng/ml. DeGroot et al., *Endocrinology* 3(9):2171-223 (1994).

The dosage of the estrogen may be selected for an individual patient depending upon the route of administration, severity of disease, age and weight of the patient, other medications the patient is taking and other factors normally considered by the attending physician, when determining the individual regimen and dosage level as the most appropriate for a particular patient. Furthermore, the exact individual dosages can be adjusted somewhat depending on a variety of factors including the specific combination of the agents being administered, the time of administration, the route of administration, the nature of the formulation, the rate of excretion, the particular disease being treated, the severity of the disorder, and the anatomical location of the disorder. Some variations in the dosage can be expected. In vitro or in vivo assays can be employed to help identify optimal dosage ranges.

The therapeutically effective dose of the estrogen included in the dosage form is selected at least by considering the type of estrogen selected and the mode of administration. The dosage form may include the estrogen in combination with other inert ingredients, including adjuvants and pharmaceutically acceptable carriers for the facilitation of dosage to the patient as known to those skilled in the pharmaceutical arts. The dosage form may be any form suitable to cause the estrogen to enter into the tissues of the patient.

Pharmaceutically acceptable carriers can optionally comprise a suitable amount of a pharmaceutically acceptable excipient so as to provide the form for proper administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can include, for example, saline, gum acacia, gelatin, starch paste, talc, keratin, colloidal silica, urea and the like. In addition, auxiliary stabilizing, thickening, lubricating, and coloring agents can be used. In one embodiment, the pharmaceutically acceptable excipients are sterile when administered to a subject. Suitable pharmaceutical excipients also include starch, glucose, lactose, sucrose, gelatin, mall, rice, flour, chalk, silica gel, sodium stearate, glycerol monostearate, talc, sodium chloride, dried skim milk, glycerol, propylene glycol water, ethanol and the like. Any agent described herein, if desired, can also comprise minor amounts of wetting or emulsifying agents, or pH buffering agents.

In one embodiment, the dosage form of the estrogen is an oral preparation (liquid, tablet, capsule, caplet, or the like) which when consumed results in elevated serum estrogen levels. The oral preparation may comprise conventional carriers including diluents, binders, time-release agents, lubricants, and disintegrates.

In other embodiments of the invention, the dosage form of the estrogen may be provided in a topical preparation (lotion, cream, ointment, patch, or the like) for transdermal application.

Alternatively, the dosage form may be provided as a suppository or the like for transvaginal or transrectal application.

However, in other embodiments, the dosage form may also allow for preparations to be applied subcutaneously, intravenously, intramuscularly, or via the respiratory system.

The term "progestogen" (also known as "gestagen") as used herein refers to any steroid hormone that binds to and activates a progesterone receptor, or a precursor thereof. The term "progestogen" thus embraces naturally occurring, synthetic, and semi-synthetic forms of progestogen, and biologically active, pharmaceutically acceptable salts and esters thereof.

In certain embodiments, the progestogen is selected from chlormadinone acetate, cyproterone acetate, desogestrel, dienogest, 5α-dihydroprogesterone, drospirenone (Yasmin®), ethanediol acetate, ethynodiol diacetate, etonogestrel (Nexplanon®), gestodene, 17-hydroxyprogesterone, levonorgestrel (Alesse®), medroxyprogesterone acetate (17α-hydroxy-6α-methylprogesterone acetate; Provera®), megestrol, megestrol acetate (17α-acetoxy-6-dehydro-6-methylprogesterone), nestorone, nomenstrol acetate, norethindrone, norethindrone acetate (also known as norethindrone acetate), norethynodrel (Enovid®), norgestimate, norgestrel, progesterone, tanaproget, trimegestone, or a pharmaceutically acceptable salt of any of the foregoing, or any combination thereof.

In certain embodiments, progestogen is a progestin. The term "progestin" as used herein refers to a synthetic progestogen as defined herein. Examples of progestins include desonestrel, dienogest, drospirenone (Yastnin®), ethanediol acetate, etonogestrel (Nexplanon®), gestodene, levonorgestrel (Alesse®), medroxyprogesterone acetate (Proverak®), nestorone, nomegestrol acetate, norethindrone, norethindrone acetate, norethynodrel (Enovid®) norgestiante norgestrel, and trimenestone.

In certain embodiments, the progestogen is selected from progesterone, 17-hydroxyprogesterone, 5α-dihydroprogesterone, norethindrone, norethindrone acetate (also known as norethindrone acetate), medroxyprogesterone acetate (17α-hydroxy-6α-methylprogesterone acetate), megestrol acetate (17α-acetoxy-6-dehydro-6-methylprogesterone), desogestrel, levonorgestrel, chlormadinone acetate, and cyproterone acetate, pharmaceutically acceptable salts of any of the foregoing, and any combination thereof. In certain embodiments, progestogen is selected from progesterone. 17-hydroxyprogesterone, 5α-dihydroprogesterone, norethindrone, norethindrone acetate (also known as norethindrone acetate), desogestrel, levonorgestrel, chlormadinone acetate, and cyproterone acetate, pharmaceutically acceptable salts and esters of any of the foregoing, and any combination thereof. In certain embodiments, progestogen is norethindrone or an ester thereof, or a pharmaceutically acceptable salt of an ester thereof, preferably norethindrone. In certain embodiments, progestogen is progesterone or an ester thereof, or a pharmaceutically acceptable salt of an ester thereof.

In certain embodiments, the progestogen is administered in a dose equal or equivalent to about 70 μg to about 7 mg norethindrone daily, such as about 100 μg to about 1 mg norethindrone daily, most preferably in a dose equal or equivalent to about 0.7 mg norethindrone daily. In certain preferred embodiments, the progestogen is norethindrone administered in a dose of 0.7 mg norethindrone daily.

In certain embodiments, the progestogen is formulated for oral administration, e.g., in a dose equal or equivalent to about 70 μg to about 7 mg norethindrone daily, such as about 100 μg to about 1 mg norethindrone daily, most preferably in a dose equal or equivalent to about 0.7 mg norethindrone daily. In certain preferred embodiments, the progestogen is norethindrone formulated for oral administration in a dose of 0.7 mg norethindrone daily.

In certain embodiments, the progestogen is orally administered in a dose equal or equivalent to about 70 μg to about 7 mg norethindrone daily, such as about 100 μg to about 1 mg norethindrone daily, most preferably in a dose equal or equivalent to about 0.7 mg (i.e., 700 μg) norethindrone daily. In certain preferred embodiments, the progestogen is norethindrone orally administered in a dose of 0.7 mg (i.e., 700 μg) norethindrone daily.

The therapeutically effective dose of the progestogen included in the dosage form can be selected at least by considering the type of progestogen selected and the mode of administration. The dosage form may include the progestogen in combination with other inert ingredients, including adjuvants and pharmaceutically acceptable carriers for the facilitation of dosage to the patient as known to those skilled in the pharmaceutical arts. The dosage form may be any form suitable to cause the progestogen to enter into the tissues of the patient.

In one embodiment, the dosage form of the progestogen is an oral preparation (liquid, tablet, capsule, caplet, or the like) which when consumed results in elevated serum progestogen levels. The oral preparation may comprise conventional carriers including diluents, binders, time-release agents, lubricants, and disintegrates.

In other embodiments of the invention, the dosage form of the progestogen may be provided in a topical preparation (lotion, cream, ointment, patch, or the like) for transdermal application.

Alternatively, the dosage form may be provided as a suppository or the like for transvaginal or transrectal application.

The estrogen is administered to the subject on a continuous basis throughout two or more consecutive treatment periods. In certain embodiments a continuous basis means daily, i.e., on consecutive days. For example, estrogen administered orally to a subject on a daily basis throughout two or more consecutive treatment periods is deemed to be estrogen administered to the subject on a continuous basis throughout two or more consecutive treatment periods. Alternatively, estrogen administered transdermally to a subject on a daily basis throughout two or more consecutive treatment periods is deemed to be estrogen administered to the subject on a continuous basis throughout two or more consecutive treatment periods.

As used herein, a "treatment period" refers to a period of time during which a subject is receiving, on a continuous or daily basis, at least one therapeutic agent administered for the purpose of treating MS in the subject. In certain embodiments, each treatment period is at least 28 consecutive days. In certain embodiments, each treatment period is at least 56 consecutive days. In certain embodiments, each treatment period is at least 84 consecutive days. In certain embodiments, each treatment period is at least 112 consecutive days. In certain embodiments, each treatment period is at least 140 consecutive days. In certain embodiments, each treatment period is at least 168 consecutive days.

In certain embodiments, each treatment period is at least 4 consecutive weeks. In certain embodiments, each treatment period is at least 8 consecutive weeks. In certain embodiments, each treatment period is at least 12 consecutive weeks. In certain embodiments, each treatment period is at least 16 consecutive weeks. In certain embodiments, each treatment period is at least 20 consecutive weeks. In certain embodiments, each treatment period is at least 24 consecutive weeks.

In certain embodiments each treatment period is at least one month. In certain embodiments, each treatment period is at least two consecutive months. In certain embodiments, each treatment period is at least three consecutive months. In certain embodiments, each treatment period is at least four consecutive months. In certain embodiments, each treatment period is at least five consecutive months. In certain embodiments, each treatment period is at least six consecutive months.

The progestogen is administered to the subject for only a portion of each treatment period. As used herein, "for only a portion of each treatment period" refers generally to a period of time that occurs during, but is at least one day shorter than a treatment period. In a preferred embodiment, the phrase "for only a portion of each treatment period" refers generally to a period of consecutive days that occurs during but is at least one day shorter than a treatment period.

In certain embodiments, the portion of each treatment period is daily for all but at least 7 consecutive days of each treatment period. For example if the treatment period is 28 days, in various embodiments the portion of such treatment period can be 1, 2, 3, 4, 5, 6, 7, 8, 9, 10, 11, 12, 13, 14, 15, 16, 17, 18, 19, 20, or 21 consecutive days. For convenience, such portion can begin on day 1 of a treatment period, such that, for this example, the portion can encompass day 1 or days 1 to 2, 1 to 3, 1 to 4, 1 to 5, 1 to 6, 1 to 7, 1 to 8, 1 to 9, 1 to 10, to 11, 1 to 12, 1 to 13, 1 to 14, 1 to 15, 1 to 16, 1 to 17, 1 to 18, 1 to 19, 1 to 20, or 1 to 21.

In certain embodiments, the portion of each treatment period is daily for all but at least 14 consecutive days of each treatment period. For example, if the treatment period is 28 days, in various embodiments the portion of such treatment period can be 1, 2, 3, 4, 5, 6, 7, 8, 9, 10, 11, 12, 13, or 14 consecutive days. For convenience, such portion can begin on day 1 of a treatment period, such that, for this example, the portion can encompass day 1 or days 1 to 2, 1 to 3, 1 to 4, 1 to 5, 1 to 6, 1 to 7, 1 to 8, 1 to 9, 1 to 10, 1 to 11, 1 to 12, 1 to 13, or 1 to 14.

In certain embodiments, the portion of each treatment period is daily for up to 7 consecutive days of each treatment period. For example, if the treatment period is 28 days, in various embodiments the portion of such treatment period can be 1, 2, 3, 4, 5, 6, or 7 consecutive days. For convenience, such portion can begin on day 1 of a treatment period, such that, for this example, the portion can encompass day 1 or days 1 to 2, 1 to 3, 1 to 4, 1 to 5, 1 to 6, or 1 to 7.

In certain embodiments the portion of each treatment period is daily for up to 14 consecutive days of each treatment period. For example, if the treatment period is 28 days, in various embodiments the portion of such treatment period can be 1, 2, 3, 4, 5, 6, 7, 8, 9, 10, 11, 12, 13, or 14 consecutive days. For convenience, such portion can begin on day 1 of a treatment period, such that, for this example, the portion can encompass day 1 or days 1 to 2, 1 to 3, 1 to 4, 1 to 5, 1 to 6, 1 to 7, 1 to 8, 1 to 9, 1 to 10, to 11, 1 to 12, 1 to 13, or 1 to 14.

In certain embodiments the portion of each treatment period is daily for all but at least half of each treatment period. For example, if the treatment period is 28 days, in various embodiments the portion of such treatment period can be 1, 2, 3, 4, 5, 6, 7, 8, 9, 10, 11, 12, 13, or 14 consecutive days. For convenience, such portion can begin on day 1 of a treatment period, such that, for this example, the portion can encompass day 1 or days 1 to 2, 1 to 3, 1 to 4, 1 to 5, 1 to 6, 1 to 7, 1 to 8, 1 to 9, 1 to 10, 1 to, 11, 1 to 12, 1 to 13, or 1 to 14.

Preferably the progestogen is administered to the subject for only a portion of each treatment period. During the remainder of the treatment period, in certain embodiments the subject can receive estrogen but neither progestogen nor a placebo in place of the progestogen. Alternatively, during the remainder of the treatment period, in certain embodiments the subject can receive both estrogen and a placebo in place of the progestogen.

An aspect of the invention is a method of treating multiple sclerosis. The method includes the steps of administering orally to a subject in need thereof, on a continuous basis for 84 consecutive days (12 weeks), about 8 mg of estriol daily; and administering orally to the subject, for 14 consecutive days (2 weeks) of the 84 consecutive days (12 weeks), about 0.7 mg of progestogen daily. In certain embodiments, the 14 consecutive days (2 weeks) are the first 14 consecutive days (2 weeks) of the 84 consecutive days (12 weeks). That is, if the 84 consecutive days of estrogen administration are deemed to start on day 1, the progestogen is administered on days 1, 2, 3, 4, 5, 6, 7, 8, 9, 10, 11, 12, 13, and 14, and then stopped. In certain embodiments, the subject may then continue to receive estrogen but neither progestogen nor a placebo in place of the progestogen for the remaining 70 days. In other embodiments, the method further includes the step of administering to the subject a placebo in place of the progestogen on each of the days the progestogen is not administered to the subject. That is, the subject may then receive both estrogen and a placebo in place of the progestogen for the remaining 70 days.

An aspect of the invention is a method of treating multiple sclerosis. The method includes the steps of administering orally to a subject in need thereof, on a continuous basis for 84 consecutive days (12 weeks), about 8 mg of estriol daily; and administering orally to the subject, for 14 consecutive days (2 weeks) of the 84 consecutive days (12 weeks), about 0.7 mg of norethindrone daily. In certain embodiments, the 14 consecutive days (2 weeks) are the first 14 consecutive days (2 weeks) of the 84 consecutive days (12 weeks). That is, if the 84 consecutive days of estrogen administration are deemed to start on day 1, the norethindrone is administered on days 1, 2, 3, 4, 5, 6, 7, 8, 9, 10, 11, 12, 13, and 14, and then stopped. In certain embodiments, the subject may then continue to receive estrogen but neither norethindrone nor a placebo in place of the norethindrone for the remaining 70 days. In other embodiments, the method further includes the step of administering to the subject a placebo in place of the norethindrone on each of the days the norethindrone is not administered to the subject. That is, the subject may then receive both estrogen and a placebo in place of the norethindrone for the remaining 70 days.

The term "subject" as used herein refers to a living mammal and may be interchangeably used with the term "patient". In certain embodiments, the subject is a human. Preferably, the human subject is female, such as a woman. In certain embodiments, the subject is a premenopausal or perimenopausal woman. In certain embodiments, the subject is a premenopausal woman. In certain embodiments, the subject is a perimenopausal woman. In certain embodiments, the subject is a postmenopausal woman.

In certain embodiments, the multiple sclerosis is relapsing-remitting multiple sclerosis. In certain embodiments, the multiple sclerosis is secondary-progressive multiple sclerosis. In certain embodiments, the multiple sclerosis is primary-progressive multiple sclerosis. In certain embodiments, the multiple sclerosis is progressive-relapsing multiple sclerosis. In certain embodiments, the subject has a mild form of any one of the foregoing subtypes of MS. In certain embodiments, the subject has a moderate form of any one of the foregoing subtypes of MS. In certain embodiments, the subject has an aggressive form of any one of the foregoing subtypes of MS.

In certain embodiments, the multiple sclerosis is, more accurately, so-called clinically isolated syndrome (CIS). Estriol can be used, in accordance with the invention, to prevent or delay the onset of relapsing-remitting MS in subjects having CIS.

The various methods disclosed herein can be methods for improving walking, vision, balance, cognition, or other symptoms in a subject, such as a subject with multiple sclerosis, and/or methods for improving multiple sclerosis functional composite (MSFC), EDSS, or MSSS scores in a subject, such as a subject with multiple sclerosis. Thus, in certain embodiments, the methods of treatment disclosed herein include methods for stabilizing or improving disability in a patient, whereby the patient's disability score (as measured by either of these tests or another suitable test) after six months, one year, or two years of therapy is at least about 10%, at least about 25%, at least about 40%, at least about 50%, or even at least about 60% higher relative to a control patient not receiving the estrogen/progestogen therapy (but otherwise receiving the same treatment as the estrogen-treated patient). Alternatively, the patient's disability score (as measured by either of these tests or another suitable test) after six months, one year, or two years of therapy is within about 2% or within about 5% of an earlier assessment, or at least about 2%, at least about 5%, at least about at least about 10%, at least about 25%, at least about 40%, at least about or even at least about 60% higher than the earlier assessment.

For example, progression of a walking disability can be tested using a walking test, e.g., assessing the subject's performance on a 25-foot walk test at different points in time, such as at 0 months (baseline), 6 months, 1 year, and 2 years. In certain embodiments, if there is documented worsening in walking (takes more seconds) by 20 percent as compared to baseline (optionally if this worsening is confirmed on a subsequent walk test (e.g., 3 months later)), then the subject is deemed to have progressive worsening in walking. For such a patient not already receiving estrogen/progestogen therapy, the subject demonstrating the progressive walking disability commences treatment with estrogen, e.g., estriol. The walking test may be repeated (e.g., at 1 year and/or 2 years from the start of estrogen treatment) to assess whether the estrogen treatment slowed or halted any further worsening in walking performance, e.g., as measured by the walking test.

Improvements in cognition outcomes associated with MS therapy, whether slowing of cognitive decline, stabilization of cognitive decline, or improvement of cognitive function, can be assessed using the PASAT (e.g., PASAT 2 or PASAT 3) or SDMT test, or alternatively the MS-COG test (see Erlanger et al., J. Neuro Sci 340: 1.23-129 (2014)). Thus, in certain embodiments, the methods of treatment disclosed herein include methods for stabilizing or improving cognition in a patient, whereby the patient's cognition outcome after one year of therapy is at least about 2%, at least about 5%, at least about 10%, at least about 25%, at least about 40%, at least about 50%, or even at least about 60% higher relative to a control patient not receiving the estrogen/progestogen therapy (but otherwise receiving the same treatment as the estrogen-treated patient), e.g., as measured by any of the preceding tests. Alternatively, the patient's cognition outcome after six months, one year, or two years of therapy may be within about 2% or within about 5% of an earlier assessment, or at least about 2%, at least about 5%, at least about 10%, at least about 25%, at least about 40%, at least about 50%, or even at least about 60% higher than the earlier assessment, e.g., as measured by any of the preceding tests at different times.

For example, a subject who scores below 50 on PASAT (and optionally if such low score is verified upon a second subsequent test, such as within one week to one month of the first) may be deemed to have cognitive disability. For such a patient not already receiving estrogen/progestogen therapy, the subject demonstrating the cognitive disability may commence treatment with estrogen, e.g., estriol. In certain embodiments, the cognitive test may be repeated (e.g., at about six months from the start of estrogen treatment) to assess whether the estrogen treatment slowed or halted any further worsening in cognitive performance, e.g., as measured by the PASAT test. In certain such embodiments, the patient's score may increase by at least 3 points over the course of six to twelve months of estrogen therapy.

While the various methods disclosed herein are typically efficacious when administered without additional therapeutics, in certain embodiments, any of these methods further includes the step of administering to the subject an immunotherapeutic agent, wherein the immunotherapeutic agent is neither an estrogen nor a progestogen. That is, in certain embodiments the subject is administered, in addition to the estrogen and progestogen (or placebo), a third agent useful in the treatment of MS. Such agents useful in the treatment of MS are, in general, immunotherapeutic agents. At least in connection with MS, such agents are sometimes referred to as disease-modifying therapies or disease-modifying therapeutics (DMTs).

The term "immunotherapeutic agent" as used herein refers to a compound with an objectively measurable effect on at least one aspect of the immune system or an immune response. In certain embodiments, the immunotherapeutic agent is immunosuppressive, i.e., it exerts an objectively measurable inhibitory effect on at least one aspect of the immune system or an immune response. In certain embodiments, the immunotherapeutic agent is anti-inflammatory. In certain embodiments, the immunotherapeutic agent is a small molecule (molecular weight less than or equal to about 1.5 kDa) pharmaceutical compound or composition. In certain embodiments, the immunotherapeutic agent is a biological compound or composition, e.g., an antibody, peptide, nucleic acid, etc.

In certain embodiments, the immunotherapeutic agent is not an estrogen. In certain embodiments, the immunotherapeutic agent is not a progestogen. Preferably, the immunotherapeutic agent is neither an estrogen nor a progestogen.

In certain embodiments, the immunotherapeutic agent is selected from dimethyl fumarate (Tecfidera®; BG-12, which may be administered in an amount from about 220 mg to about 260 mg per day, such as about 220 mg, 240 mg, or 260 mg per day), fingolimod (Gilenya®, which may be administered in an amount from about 0.25 mg to about 0.75 mg per day, such as about 0.25 mg, 0.50 mg, or 0.75 mg per day), glatiramer acetate (Copaxone®, for example "longer-lasting" 40 mg/ml or 20 mg/ml versions), interferon beta-1a (Avonex® or Rebif®), interferon beta-1b (Betaseron® or Extavia®), mitoxantrone (Novantrone®), natalizumab (Tysabri®) and teriflunomide (Aubagio®, which may be administered in an amount from about 7 mg to about 14 mg per day, such as about 7 mg, 10 mg, or 14 mg per day), mycophenolate mofetil, paclitaxel, cyclosporine, corticosteroids (e.g., prednisone, methylprenisolone), azathioprine, cyclophosphamide, methotrexate, eladribine, 4-aminopyridine, and tizanidine. In certain embodiments, the immunotherapeutic agent is selected from dimethyl fumarate (Teefidera® BG-12), fingolimod (Gilenya®), glatiramer acetate (Copaxone®), interferon beta-1a (Avonex® or Rebif®), interferon beta-1b (Betaseron® or Extavia®), mitoxantrone (Novantrone®), natalizumab (Tysabri®), and teriflunomide (Aubagio®).

In certain embodiments, the immunotherapeutic agent is dimethyl fumarate (Tecfidera® BG-12). In certain embodiments, the immunotherapeutic agent is fingolimod (Gilenya®). In certain embodiments, the immunotherapeutic agent is glatiramer acetate (Copaxone®). In certain embodiments, the immunotherapeutic agent is interferon beta-1a (Avonex® or Rebif®). In certain embodiments, the immunotherapeutic agent is interferon beta-1b (Betaseron® or Extavia®). In certain embodiments, the immunotherapeutic agent is mitoxantrone (Novantrone®). In certain embodiments, the immunotherapeutic agent is natalizirmab (Tysabri®). In certain embodiments, the immunotherapeutic agent is teriflunomide (Aubagio®).

In certain embodiments, the subject is already receiving a disease-modifying therapeutic. In this circumstance, the subject can continue to receive the disease-modifying therapeutic while taking the estrogen, with and without the progestogen. Significantly, however, the dose of the disease-modifying therapeutic may be decreased when used in combination with the estrogen, with and without the progestogen. For example, a current standard dose for glatiramer acetate (Copaxone®) is 40 mg subcutaneously (s.c.) three times a week, or 20 mg s.c. daily. In conjunction with estrogen and progestogen in accordance with the invention, the dose for glatiramer acetate (Copaxone®) may be reduced by up to 50 percent or more, e.g., to 20 mg s.c. three times a week.

As another example, a current standard dose for fingolimod (Gilenya®) is 0.5 mg by mouth (p.o.) daily. In conjunction with estrogen and progestogen in accordance with the invention, the dose for fingolimod (Gilenya®) may be reduced by up to 50 percent or more, e.g., to 0.25 mg p.o. daily.

As another example, a current standard dose for dimethyl fumarate (Tecfidera®) is 240 mg p.o. daily. In conjunction with estrogen and progestogen in accordance with the invention, the dose for dimethyl fumarate (Tecfidera®) may be reduced by up to 50 percent or more, e.g., to 120 mg p.o. daily.

As yet another example, a current standard dose for interferon beta-1a (Avonex® or Rebif®) is 30 µg intramuscularly (i.m.) weekly (Avonex®) or 44 µg s.c. three days a week (Rebif®). In conjunction with estrogen and progestogen in accordance with the invention, the dose for Avonex® may be reduced to 15 µg i.m. weekly, and the dose for Rebif® may be reduced to 22 µg s.c. three days a week.

As yet another example, a current standard dose for interferon beta-1b (Betaseron® or Extavia®) is 0.25 mg s.c. every other day (Betaseron® or Extavia®). In conjunction with estrogen and progestogen in accordance with the invention, the dose for interferon beta-1b (Betaseron® or Extavia®) may be reduced to 0.125 mg s.c. every other day.

In certain embodiments, the subject is receiving an immunotherapeutic agent and has cognitive disability. For example, if a subject scores below 50 on PASAT, and optionally if such low score is verified upon retest within about one week to one month, then the subject may be deemed to have cognitive disability. In accordance with the invention, this cognitive disability is treated with estrogen, e.g., estriol, and, in certain embodiments, followed up with further retest e.g., about six months from the start of estrogen treatment, such as to achieve an increase in test score of at least 3 points.

In certain embodiments, the subject is receiving an immunotherapeutic agent and has progressive walking disability. For example, the subject performs a 25 foot walk test, e.g., at 0 months (baseline), 6 months, 1 year, and/or 2 years. If there is documented worsening in walking (takes more seconds), e.g., by 20 percent as compared to baseline, and this worsening is confirmed on a repeated walk test, e.g., about 3 months later, then the subject is deemed to have progressive worsening in walking. In accordance with the invention, this progressive walking disability is treated with estrogen, e.g., estriol, and, in certain embodiments, followed up with repeat walking test, at about 1 year or 2 years from the start of estrogen treatment, such as to stabilize or halt any further worsening in walking times.

In certain embodiments, the subject is receiving an immunotherapeutic agent and experiencing a relapse or progression of the multiple sclerosis. For example, a subject may experience a relapse or progression while on a maintenance dose of a DMT. Such subject can then begin concurrent treatment with estrogen in accordance with any of the various methods disclosed herein, e.g., to reduce the frequency and/or severity of relapses or to slow progression of the disease (e.g., as determined by assessment of one or more of walking, vision, balance, cognition, or other symptoms of the condition, e.g., as measured according to the Expanded Disability Severity Scale (EDSS) and/or the multiple sclerosis functional composite (MSFC)). Thus, the various embodiments of the methods disclosed herein can be methods for improving walking, vision, balance, cognition, or other symptoms in a subject, such as a subject with multiple sclerosis, and/or methods for improving EDSS or MSFC scores in a subject, such as a subject with multiple sclerosis.

In certain embodiments, the subject is receiving an immunotherapeutic agent and experiencing a relapse of the multiple sclerosis. For example, a subject may experience a relapse while on a maintenance dose of a DMT. Such subject can then begin concurrent treatment with estrogen in accordance with a method of the present invention, e.g., to reduce the frequency and/or severity of relapses.

In certain embodiments, the subject is receiving an immunotherapeutic agent selected from interferon-beta 1a, interferon-beta 1b, glatiramer acetate, natalizumab, mitoxantrone, fingolimod, teriflunomide, and dimethyl fumarate during a ramp-up period for dose of the immunotherapeutic agent, e.g., the patient begins receiving the immunotherapeutic and the estrogen therapy at the same time or at about the same time (such as for patients who have not previously received treatments for their disease). Advantageously, estrogen induces a rapid onset of therapeutic effect on MS, while commonly an immunotherapeutic agent such as interferon-beta 1a, interferon-beta 1b, glatiramer acetate, natalizumab, mitoxantrone, fingolimod, teriflunomide, or dimethyl fumarate may take weeks to months to induce observable improvements on some or all symptoms.

In certain embodiments, the subject is receiving glatiramer acetate during a ramp-up period for dose of the glatiramer acetate. In other certain embodiments, the subject is not already receiving a disease-modifying therapeutic.

In certain embodiments, the estrogen and the progestogen are formulated separately from one another, e.g., the subject receives the estrogen as a single formulation and the progestogen as a separate formulation. For oral administration, a given dose of each formulation can comprise one or more pills, tablets, capsules, or the like (i.e., unit doses). For example, an 8 mg dose of estriol can be administered as four 2 mg capsules, and a 0.7 mg dose of norethindrone can be administered as a single capsule, though preferably each dose is administered in a single unit dose (e.g., one unit dose each for the estrogen and the progestogen).

In certain embodiments, e.g., where a placebo is administered with the estrogen on days when progestogen is not administered, the estrogen and the placebo are formulated separately from one another. For example, the subject is administered the estrogen as a single formulation and the placebo as a separate formulation. For oral administration, a given dose of each formulation can comprise one or more pills, tablets, capsules, or the like (i.e., unit doses). For example, an 8 mg dose of estriol can be administered as four 2 mg capsules, and a placebo can be administered as a single capsule.

When a given dose of any agent involves administration of more than a single unit dose, e.g., four 2 mg capsules of estriol, the individual unit doses can be administered at essentially the same time, or they can be administered at different times on a given day, provided the entire daily dose is administered within a single day. For example, four 2 mg capsules of estriol can be taken together essentially once a day, or they may be taken two at a time twice a day, or they may be taken one at a time four times a day. Additional schedules are contemplated by the invention, again provided the entire daily dose is administered within a single day. While it may be preferable that the subject follow the same schedule from one day to the next, such is not required, once again provided the entire daily dose is administered within a single day.

When the estrogen and the progestogen are formulated separately, they can be administered essentially simultaneously, or they can be administered sequentially with respect to each other. For example, in one embodiment the subject is administered four 2 mg capsules of estriol and one 0.7 mg capsule of norethindrone essentially simultaneously. In another embodiment, the subject is administered estriol in divided doses, e.g., two 2 mg capsules twice daily, and the progestogen is administered essentially simultaneously with one of the divided doses of estriol. In yet another embodiment, the subject is administered estriol in divided doses, e.g., two 2 mg capsules twice daily, and the progestogen is administered at a separate time from either one of the divided doses of estriol.

Similarly, when the estrogen and the placebo are formulated separately, they can be administered essentially simultaneously, or they can be administered sequentially with respect to each other. For example, in one embodiment the subject is administered four 2 mg capsules of estriol and one placebo essentially simultaneously. In another embodiment, the subject is administered estriol in divided doses, e.g., two 2 mg capsules twice daily, and the placebo is administered essentially simultaneously with one of the divided doses of estriol. In yet another embodiment, the subject is administered estriol in divided doses, e.g., two 2 mg capsules twice daily, and the placebo is administered at a separate time from either one of the divided doses of estriol.

In certain embodiments, the estrogen and the progestogen are formulated together. For oral administration, a given dose of each component, formulated together, can comprise one or more pills, tablets, capsules, or the like (i.e., unit doses). For example, an 8 mg dose of estriol and a 0.7 mg dose of norethindrone can be coformulated and administered as four capsules, each containing 2 mg estriol and 0.0875 mg norethindrone, though preferably, where applicable, they are coformulated as one unit dose comprising both the estrogen and the progestogen.

In certain embodiments, e.g., where a placebo is administered with the estrogen on days when progestogen is not administered, the estrogen and the placebo are formulated together. For oral administration, a given dose of each component, formulated together, can comprise one or more pills, tablets, capsules, or the like (i.e., unit doses). For example, an 8 mg dose of estriol and a placebo can be coformulated and administered as four capsules, each containing 2 mg estriol and a suitable amount of placebo.

When a given dose of any coformulation of estriol and progestogen (or placebo) involves administration of more than a single unit dose, e.g., four capsules, each containing 2 mg estriol and 0.0875 mg norethindrone, the individual unit doses can be administered at essentially the same time, or they can be administered at different times on a given day, provided the entire daily dose is administered within a single day. For example, four capsules, each containing estriol and progestogen (or placebo) can be taken together essentially once a day, or they may be taken two at a time twice a day, or they may be taken one at a time four times a day. Additional schedules are contemplated by the invention, again provided the entire daily dose is administered within a single day. While it may be preferable that the subject follow the same schedule from one day to the next, such is not required, once again provided the entire daily dose is administered within a single day.

Clinically, MS can be assessed and monitored using any of a number of structural (anatomical) and functional tests, including, without limitation: magnetic resonance imaging (MRI); Paced Serial Addition Test (PASAT); symbol digit modalities test (SDMT); expanded disability status score (EDSS), multiple sclerosis functional composite (MSFC); 25-foot walk test; 9-hole peg test; low contrast visual acuity; MS Quality of Life; Modified Fatigue Impact Scale; Beck Depression Inventory; 7/24 Spatial Recall Test; Benton Forms F & G; Buschke Selective Reminding Test; Verbal Paired Associates; Word List Generation. Recently, the PASAT test of cognitive function has come under criticism by some for its test-retest reliability and practice effect whereby one naturally improves over time with repeated test taking, Polman C H et al., *Neurology* 74 Suppl 3: S8-15 (2010). In some embodiments, assessment of MacDonald dissemination in space and time finds use in the present methods. For example, for dissemination in space, lesion imaging, such as, by way of illustration, Barkhof-Tintore MR imaging criteria, may be used. For instance, the following criteria can be evaluated: (1) at least one gadolinium-enhancing lesion or 9 T2 hyperintense lesions; (2) at least one infratentorial lesion; (3) at least one juxtacortical lesion; (4) at least 3 periventricular lesions; and (5) a spinal cord lesion. Such imaging criteria can optionally be used in combination with evaluation for immunoglobulin abnormalities in the cerebrospinal fluid (CSF), for example. For dissemination in time, MR imaging can also be used. For example, if an MR imaging scan of the brain performed at ≥3 months after an initial clinical event demonstrates a new gadolinium-enhancing lesion, this may indicate a new CNS inflammatory event, because the duration of gadolinium enhancement in MS is usually less than 6 weeks. If there are no gadolinium-enhancing lesions but a new T2 lesion (presuming an MR imaging at the time of the initial event), a repeat MR imaging scan after another 3 months may be needed with demonstration of a new T2 lesion or gadolinium-enhancing lesion. In various embodiments, any one or more of these structural (anatomical) and functional tests may be used in conjunction with the present invention (e.g., to assess the effectiveness of a disclosed treatment method).

A randomized, double-blind, placebo-controlled clinical trial was designed to ascertain whether, in women, treatment with an estrogen pill (estriol), used in combination with major FDA-approved standard treatments for MS (Betaseron®, Extavia®, Rebif®, Avonex®, Copaxone®, Gilenya®, Aubagio®, or Tecfidera®) for one year, can improve cognitive testing as compared to treatment with a placebo pill in combination with the same major FDA-approved standard treatments for MS. Interim results from this study are presented in the Examples below.

With respect to the estriol intervention, the study design includes continuous treatment with estriol, part of the time with norethindrone, and part of the time without norethindrone. That is, again with respect to the estriol intervention, the study can be understood as a series of consecutive periods, wherein for each period the subject continuously receives estriol and, for only a portion of each period, the subject also receives norethindrone.

In the experimental group, subjects receive standard MS treatment plus estriol 8 mg by mouth daily (continuously) plus norethindrone 0.7 mg by mouth daily for two weeks starting at month 6 and at months 9 and 12.

In the control group, subjects receive standard MS treatment plus estriol placebo by mouth daily (continuously) plus norethindrone placebo by mouth daily for two weeks starting at month 6 and at months 9 and 12.

Study subjects are 18- to 50-year-old women with diagnosis of clinically definite or MacDonald criteria relapsing-remitting MS, secondary-progressive MS, or primary-progressive MS: on a stable dose of Copaxone®, Betaseron®, Extavia®, Rebif®, Avonex®, Gilenya®, Aubagio®, or Tecfidera® for a minimum of 3 months duration prior to enrollment; and with no relapse within 30 days before trial enrollment. Excluded from the study are women on oral contraceptives (OCP), hormone replacement therapy (HRT), progesterone intrauterine devices (IUDs), or other sex hormones.

The primary outcome measure for this study is change from baseline in cognitive function (processing speed), assessed by Paced Serial Addition Test (PASAT). Numerical test scores (ranging from 0-60) are acquired, then percent change for each subject at trial conclusion as compared to baseline is determined. A primary goal is to determine whether greater improvement as expressed as percent change occurs in the estriol group as compared to the placebo group.

Secondary outcome measures include change from baseline in cognitive function as assessed by cognitive evoked potentials, measured in milliseconds; change from baseline in standard MS outcome measures (relapses, expanded disability status score (EDSS), 25-foot walk test, 9-hole peg test, low contrast visual acuity, MS Quality of Life, Modified Fatigue Impact Scale, and Beck Depression Inventory); change from baseline in cognitive function as assessed by a brief battery of cognitive tests; and safety.

Cognitive evoked potentials are recorded in msecs for each subject at baseline and conclusion. The percent improvement at conclusion as compared to baseline for each subject is determined. Group comparisons will reveal whether the percent improvement is greater in the estriol treated group as compared to the placebo treated group.

A brief battery of cognitive tests is administered, including: Processing speed: symbol digit modalities test (SDMT); Visual memory: 7/24 Spatial Recall Test, Benton Forms F & G; Verbal memory: Buschke Selective Reminding Test, Verbal Paired Associates: and Language: Word List Generation. Each subject is tested at baseline, month 6, and conclusion. Percent change at conclusion as compared to baseline is determined in each subject. Group comparisons will reveal which cognitive test within the battery had greater improvement in the estriol treated group as compared to the placebo treated group.

Safety is measured based on neurologic exams, laboratory tests (chemistries, complete blood count (CBC)), and breast and gynecologic exams.

In some aspects, the invention relates to a method of slowing, halting, or reversing physical disability or stabilizing or improving physical disability in a female subject who has multiple sclerosis, comprising administering to the subject an estrogen and a secondary agent. The estrogen may be administered orally. The estrogen may be formulated as a pill, e.g., for oral administration. The estrogen may be administered orally in a dose equal or equivalent to about 8 mg of estriol per day. The estrogen may be estriol. Estriol may be administered at a dose sufficient to induce an estriol level in the blood that is consistent with a level observed during mid-pregnancy. Physical disability may be assessed, for example, using the expanded disability status scale ("EDSS"). The subject may have relapsing-remitting multiple sclerosis or secondary progressive multiple sclerosis. For example, the subject may have secondary progressive multiple sclerosis and the estrogen may be administered as a neuroprotective agent. The secondary agent may be glatiramer acetate copolymer 1. Glatiramer acetate copolymer 1 may be administered, for example, by injection. The estrogen and secondary agent may be administered for at least 12 months, such as for 12 months, 13 months, 14 months, 15 months, 16 months, 17 months, 18 months, 19 months, 20 months, 21 months, 22 months. 23 months, or 24 months. The estrogen and secondary agent may be administered for at least 24 months. The method may further comprise evaluating the physical disability of a subject, e.g., by obtaining an EDSS score. The method may further comprise evaluating a change in the physical disability of a subject, e.g., by obtaining a first EDSS score, obtaining a second EDSS score, and comparing the first EDSS score and the second EDSS score, thereby evaluating the change in physical disability. The first EDSS score may be obtained prior to administering the estrogen and the secondary agent, such as within a day, week, or month prior to administering the estrogen and the secondary agent. The second EDSS score may be obtained a period of time after first administering the estrogen and the secondary agent, such as at least 12 months after first administering the estrogen and the secondary agent, such as 12 months or 24 months after first administering the estrogen and the secondary agent.

In some embodiments, the invention relates to a method of slowing, halting, or reversing cognitive decline or stabilizing or improving cognitive function in a female subject who has multiple sclerosis, comprising administering to the subject an estrogen and a secondary agent. The estrogen may be administered orally. The estrogen may be formulated as a pill, e.g., for oral administration. The estrogen may be administered orally in a dose equal or equivalent to about 8 mg of estriol per day. The estrogen may be estriol. Estriol may be administered at a dose sufficient to induce an estriol level in the blood that is consistent with a level observed during mid-pregnancy. Cognitive function and or cognitive decline may be assessed, for example, using the paced auditory serial additional test ("PASAT"). The subject may have relapsing-remitting multiple sclerosis or secondary progressive multiple sclerosis. For example, the subject may have secondary progressive multiple sclerosis and the estrogen may he administered as a neuroprotective agent. The secondary agent may be glatiramer acetate copolymer 1. Glatiramer acetate copolymer 1 may be administered, for example, by injection. The estrogen and secondary agent may be administered for at least 12 months, such as for 12 months, 13 months, 14 months, 15 months, 16 months, 17 months, 18 months, 19 months, 20 months, 21 months, 22 months, 23 months, or 24 months. The estrogen and secondary agent may be administered for at least 24 months. The method may further comprise evaluating the cognitive function of a subject, e.g., by obtaining a PASAT score. The method may further comprise evaluating a change in the cognitive function of a subject, e.g., by obtaining a first PASAT score, obtaining a second PASAT score, and comparing the first PASAT score and the second PASAT score, thereby evaluating the change in cognitive function. The first PASAT score may be obtained prior to administering the estrogen and the secondary agent, such as within a day, week, or month prior to administering the estrogen and the secondary agent. The second PASAT score may be obtained a period of time after first administering the estrogen and the secondary agent, such as at least 12 months after first administering the estrogen and the secondary agent, such as 12 mouths or 24 months after first administering the estrogen and the secondary agent.

In some embodiments, the invention relates to a method of treating a human patient exhibiting a least one clinical sign or symptom of multiple sclerosis (e.g., weakness, numbness, tingling, loss of vision, memory difficulty, extreme fatigue, gadolinium enhancing lesions, the accumulation of T2 lesions, elevated Th1 cytokines (e.g., interferon gamma), and/or reduced Th2 cytokines (e.g., IL-10)), comprising administering to the patient an estriol, an immunomodulatory compound, and norethindrone. The method may ameliorate the at least one sign or symptom of multiple sclerosis. The estriol may be selected from estriol, estriol succinate, estriol sulfamate, or estriol dihexanoate. The estriol may be administered orally at a dose of about 1 mg to about 20 mg per day, such as about 4 mg to about 16 mg. For example, the estriol may be administered orally at a dose of 2 mg, 4 mg, 6 mg, 8 mg, 10 mg, 12 mg, 14 mg, or 16 mg per day. Estriol may be administered at a dose sufficient to increase the serum concentration of estriol in the patient to between about 2 ng/mL and about 30 ng/mL. The immunomodulatory compound may be administered orally. The immunomodulatory compound may be, for example, fingolimod, teriflunomide, dimethyl fumarate, or a combination thereof. For example, the immunomodulatory compound may be fingolimod, and fingolimod may be administered at a dose of about 0.25 mg to about 0.75 mg per day, such as about 0.25 mg, about 0.5 mg, or about 0.75 mg per day. In some embodiments, fingolimod is administered daily. The immunomodulatory compound may be teriflunomide, and teriflunomide may be administered at a dose of about 7 mg to about 14 mg per day, such as about 7 mg, about 10 mg, or about 14 mg per day. In some embodiments, teriflunomide is administered daily. The immunomodulatory compound may be dimethyl fumarate, and dimethyl fumarate may be administered at a dose of about 220 mg to about 260 mg per day, such as about 220 mg, about 240 mg, or about 260 mg per day. In some embodiments, dimethyl fumarate is administered twice daily. The norethindrone may be administered orally at a dose of about 0.4 mg to about 1.0 mg per day, e.g., for two weeks every three months. For example, the norethindrone may be administered orally at a dose of about 0.7 mg per day, e.g., for two weeks every three months.

Having now described the present invention in detail, the same will be more clearly understood by reference to the following examples, which are included herewith for purposes of illustration only and are not intended to limit the invention.

EXEMPLIFICATION

Example 1—Use of Copaxone® and Estriol for the Treatment of Multiple Sclerosis

This example describes a randomized, double-blind, placebo-controlled human clinical trial for the treatment of multiple sclerosis using Copaxone® and estriol.

Enrollment Criteria

Eligible patients were female, between ages 18 and 50, had active relapsing disease, and had an Expanded Disability Status Seale (EDSS) score between 0 and 4.5. Women who were pregnant, breastfeeding, taking hormone replacement therapy, or taking oral contraceptives were excluded from the trial.

Study Conduct and Monitoring Schedule 158 patients were randomized to Copaxone® (glatiramer acetate) injections (20 mg/day) and oral estriol (8 mg/day) or to Copaxone® injections and placebo for a 24-month treatment duration. Gynecologists examined the patients before, during, and after the study. Each patient was examined at three- to six-month intervals during the trial. Patients also underwent mammograms before and after the study. In addition, at baseline, three months, six months, 12 months, 18 months, and 24 months, the investigators measured participants' estriol levels, and assessed for MS relapses and MS-related disabilities.

A total of 82 patients received Copaxone® plus estriol, and 76 patients received Copaxone® plus placebo. Baseline characteristics were similar in both patient groups. Participants' mean age at entry was approximately 38, and their mean EDSS score at entry was 2.2. Estriol levels in serum were in a mid-pregnancy range in the estriol-treated group. To ensure breast and uterus safety, every three months the patients took norethindrone 0.7 mg once a day for 14 days. This hormone regimen was found to be safe and well tolerated with regard to serious adverse events, adverse events, general exams, blood chemistries, and hematological studies, as well as for gynecological outcomes (see Table 1).

finding that Copaxone® plus estriol treatment had significant benefit in reducing the frequency of relapses over 24 months, the combination treatment also had a more rapid onset of action as compared to Copaxone® plus placebo.

These results were surprising given that estriol treatment was not compared to a true placebo, but rather was tested in combination with standard-of-care therapy (Copaxone®). Since anti-inflammatory drugs the FDA has approved have so far required much larger sample sizes to show a significant reduction in relapse rates, even as compared to a true placebo, the results of the study adding estriol to Copaxone® suggest a novel mechanism of action, a mechanism never before observed in MS.

Cognitive Disability Assessment

Figure 2:
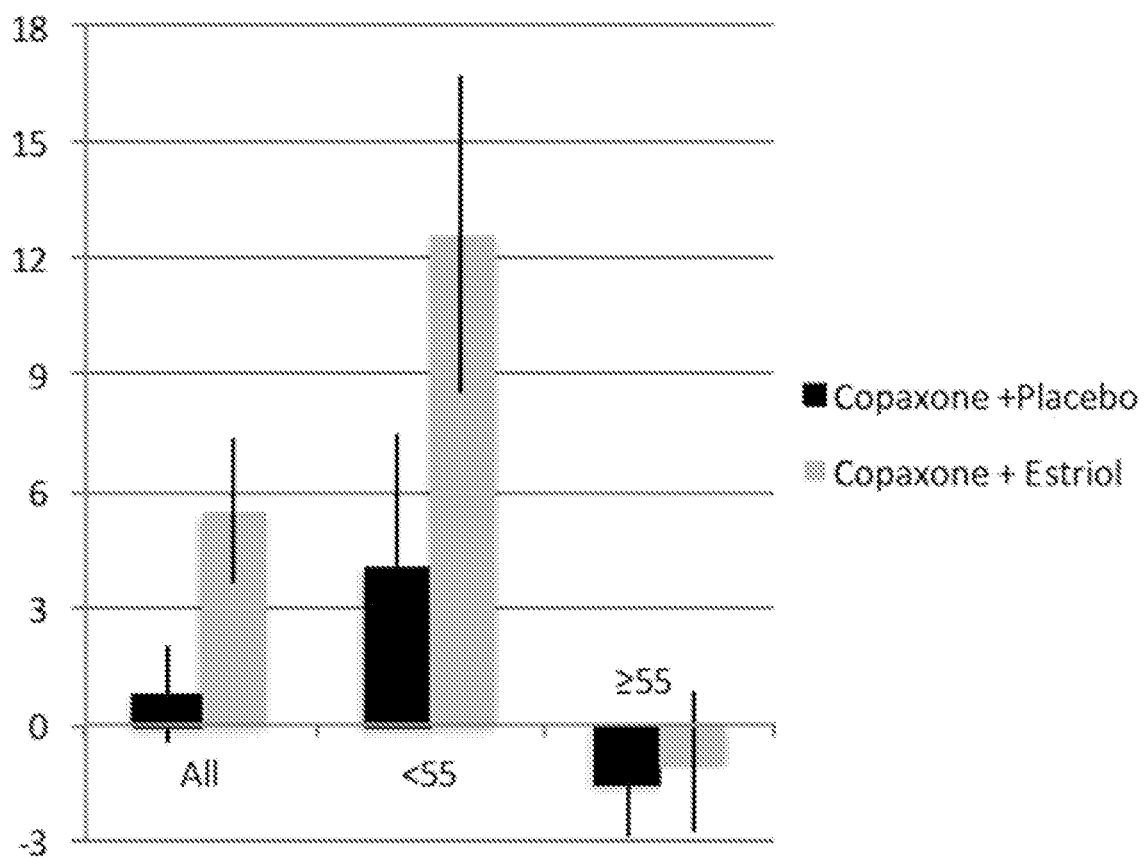
FIG. 2 is a bar graph depicting Paced Serial Addition Test (PASAT) cognitive test scores for all subjects (All), subjects with baseline scores of less than 55/60 (<55), and subjects with baseline scores greater than or equal to 55/60 (≥55). Comparison is made between treatment groups receiving Copaxone® plus estriol or Copaxone® plus estriol placebo. Data are expressed as percent change from baseline in each treatment group.

The effect of treatment was assessed on cognitive disability with a test for processing speed that has been extensively used in MS, the Paced Auditory Serial Addition Test (PASAT). A perfect score is 60, with scores lower than 55 indicating disability. By 12 months of treatment, scores on the PASAT improved by approximately 6% (i.e., 3 points), compared with scores at baseline, among patients receiving Copaxone® plus estriol (p=0.03). The change largely resulted from a 12% improvement (i.e., 6 points) among participants with cognitive disability prior to treatment as reflected in scores of less than 55 at baseline (of a maximum of 60), see FIG. 2. After 12 months of treatment, patients receiving Copaxone® plus estriol continued to have high PASAT scores to the end of study at month 24, while participants receiving placebo began to show improved PASAT scores by month 24. Notably, a change of six or more points in tests of processing speed in MS is considered

TABLE 1

Safety and Tolerability Data

| Patient Group[a] | Uterine fibroids on ultrasound | Uterine endometrial thickness > 8 mm on ultrasound | Uterine endometrial biopsies | Breast - Fibrocystic breast disease on clinical exam | Mammograms |
| --- | --- | --- | --- | --- | --- |
| Placebo | 8 subjects | 27 subjects with 41 exams | 6 subjects with 10 exams (no abnormal proliferation) | 4 subjects | No breast cancer |
| Estriol | 8 subjects | 24 subjects with 32 exams | 9 subjects with 11 exams (no abnormal proliferation) | 5 subjects | |

[a]Patients received Copaxone ® with either estriol or placebo

Primary Outcome Measure

The primary outcome measure for disease efficacy was annualized relapse rate. While most Phase II trials used surrogates or biomarkers as the primary outcome, the trial focused on an outcome measure acceptable for approval by the FDA. Since this was a Phase II trial, it was powered to reduce relapses by one third more in the Copaxone® plus estriol group as compared to the Copaxone® plus placebo group, with a targeted p value of p=0.10 at the end of study which was 24 months. As shown in FIG. 1, after 24 months of treatment the primary outcome measure was attained by reducing relapse rates by 32% (p=0.11) in the Copaxone® plus estriol group as compared to the Copaxone® plus placebo group. Surprisingly, after only 12 months of treatment, the relapse rate was reduced by 47% (p=0.02) in the Copaxone® plus estriol group as compared to the Copaxone® plus placebo group, see FIG. 1. Thus, in addition to to be clinically significant. Further, Copaxone® plus estriol treatment improved function in those with significant cognitive disability, rather than merely slowing cognitive decline. This represents repair of disability, not merely prevention of worsening.

Figure 3:
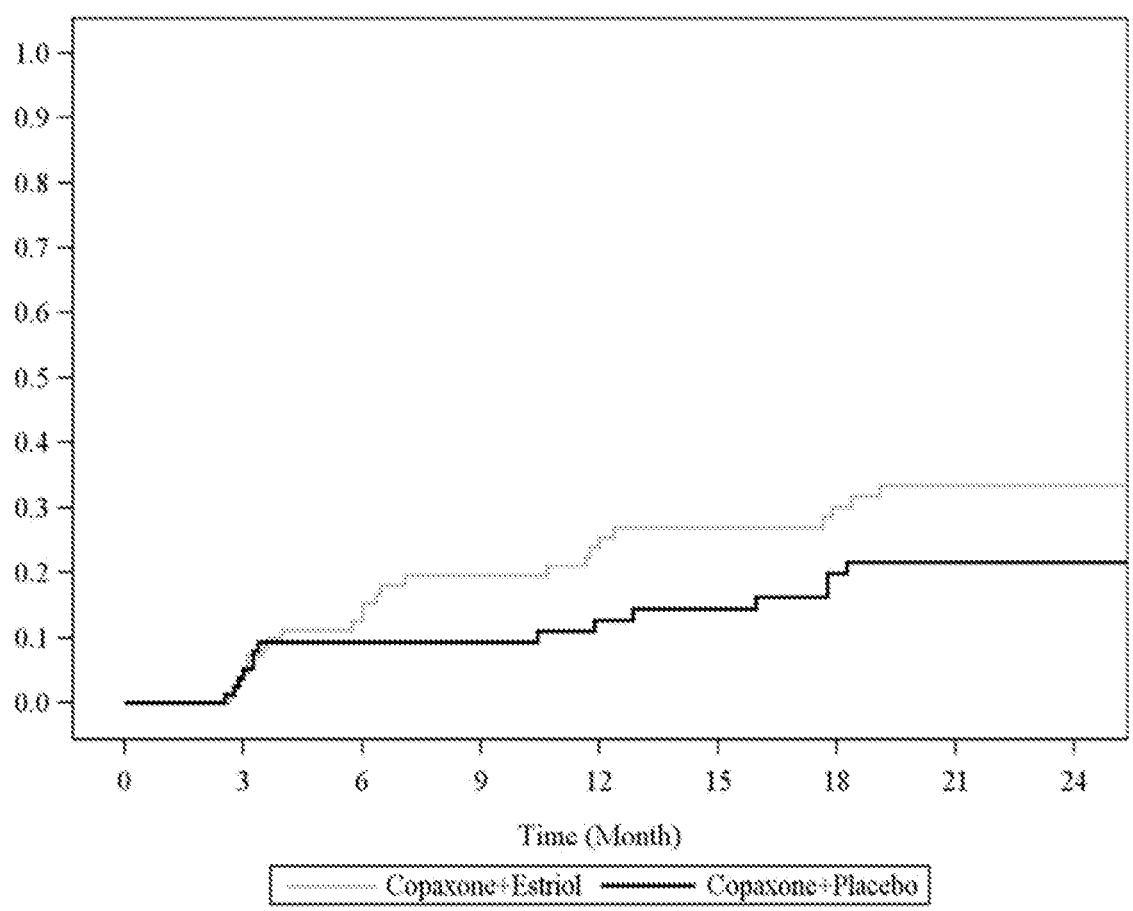
FIG. 3 is a graph depicting the proportion of all subjects who had sustained improvement of 3 points in PASAT scores for 6 months. Comparison is made between treatment groups receiving Copaxone® plus estriol (upper curve) or Copaxone® plus estriol placebo (lower curve).

Next it was shown that the improvement in PASAT cognitive test scores was sustained when subjects were followed for the entire 24 month period, p=0.02 (FIG. 3).

In addition, the beneficial effects of estriol treatment on cognitive function were shown using another cognitive test, the 7/24 spatial recall test (for spatial memory). While initial encoding of information did not differ between groups, the number of subjects with perfect scores for immediate recall (p=0.006) and delayed recall (p=0.04) was higher in the Copaxone® plus estriol treated group as compared to the Copaxone® plus placebo treated group over the entire 24 month treatment duration. Such rapid and potent effects on cognition that were observed in the Copaxone® plus estriol group as compared to the Copaxone® plus placebo group were surprising and point to a novel effect on cognitive disability not seen before with other FDA-approved MS drugs.

Ambulatory Assessment

Figure 4:
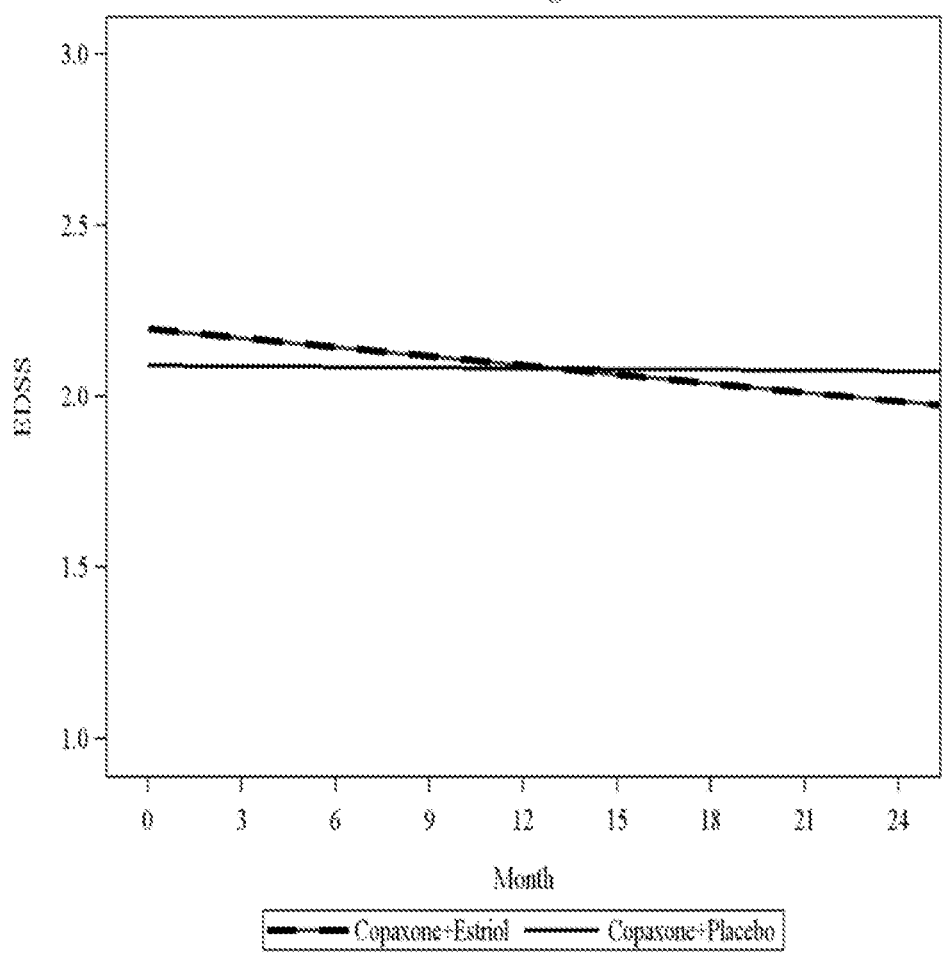
FIG. 4 is a graph depicting Expanded Disability Status Scale (EDSS) scores Over 24 months for treatment groups receiving Copaxone® plus estriol (slope=−0.11, p=0.06) or Copaxone® plus estriol placebo (slope=−0.01, p=0.90).

The Expanded Disability Status Scale (EDSS) is a standard composite disability score used in MS trials. Higher scores indicate worse disability. This composite covers a variety of disabilities (including ambulation, vision, cognition, coordination, etc.), but the scoring is not linear and the composite score is understood to be principally an indicator of the level of disability in ambulation. While there was no change in the EDSS scores for the Copaxone® plus placebo treatment group, the Copaxone® plus estriol treatment group showed a significant decrease (i.e., improvement) in this disability score (FIG. 4). Further, the probability of EDSS progression (as defined by an increase in EDSS of 1 point for over 6 months) was 19% less likely in the Copaxone® plus estriol group, while the probability of EDSS improvement (as defined by a decrease in EDSS of 1 point for over 6 months) was 23% more likely in the Copaxone® plus estriol group.

Another clinical disability measure with treatment effects was the timed 25-foot walk test. This test measures how many seconds it takes to walk 25 feet, with higher scores indicating worse disability. The walk time was significantly increased in the Copaxone® plus placebo group (p=0.03), while it was slightly decreased in the Copaxone® plus estriol group, together resulting in a significant between-group difference (p=0.02). Together these data show a gradual worsening in walking times in the Copaxone® plus placebo treated group, which did not occur in the Copaxone® plus estriol treated group. This beneficial effect of estriol treatment on 25-foot walking times is consistent with the beneficial effect of estriol treatment on EDSS scores since the latter is weighted toward being an indicator of ambulation.

Figure 5A:
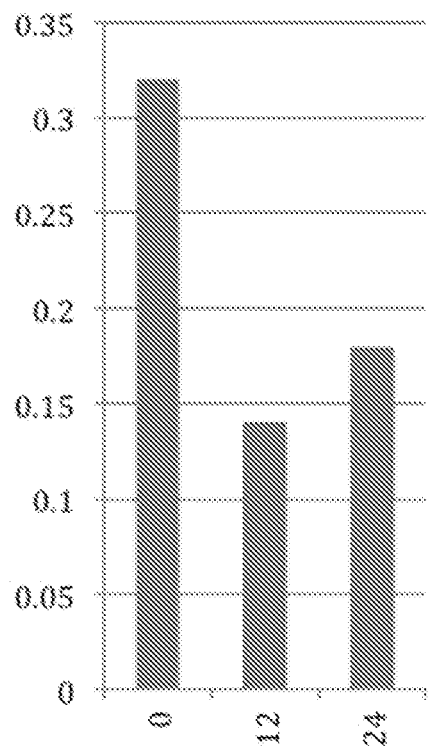
FIG. 5A is a bar graph depicting the number of subjects with brain MRIs that had enhancing lesions at 12 months in subjects receiving Copaxone® plus estriol. 0, 12, and 24 refer to months on treatment.
Figure 5B:
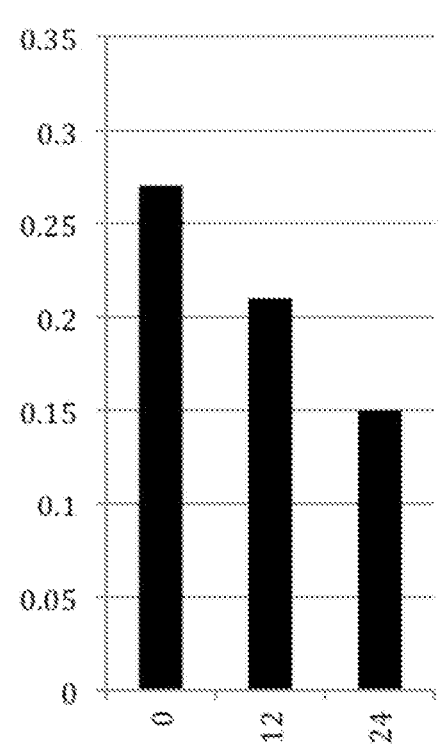
FIG. 5B is a bar graph depicting the number of subjects with brain MRIs that had enhancing lesions at 12 months in subjects receiving Copaxone® plus estriol placebo. 0, 12, and 24 refer to months on treatment.

Brain MRI is used extensively in MS as a surrogate marker for clinical effects. Brain white matter gadolinium enhancing lesions are a biomarker for relapses. It was found that the number of subjects with brain MRI scans that were positive for enhancing lesions was reduced by 56% at month 12 in the Copaxone® plus estriol treatment group vs. by 22% in the Copaxone® plus placebo treatment group (p=0.14). This effect is consistent with the observation that the Copaxone® plus estriol group demonstrated a more rapid onset of action in reducing relapse rates as compared to the Copaxone® plus placebo group (FIGS. 5A,B).

Figure 6:
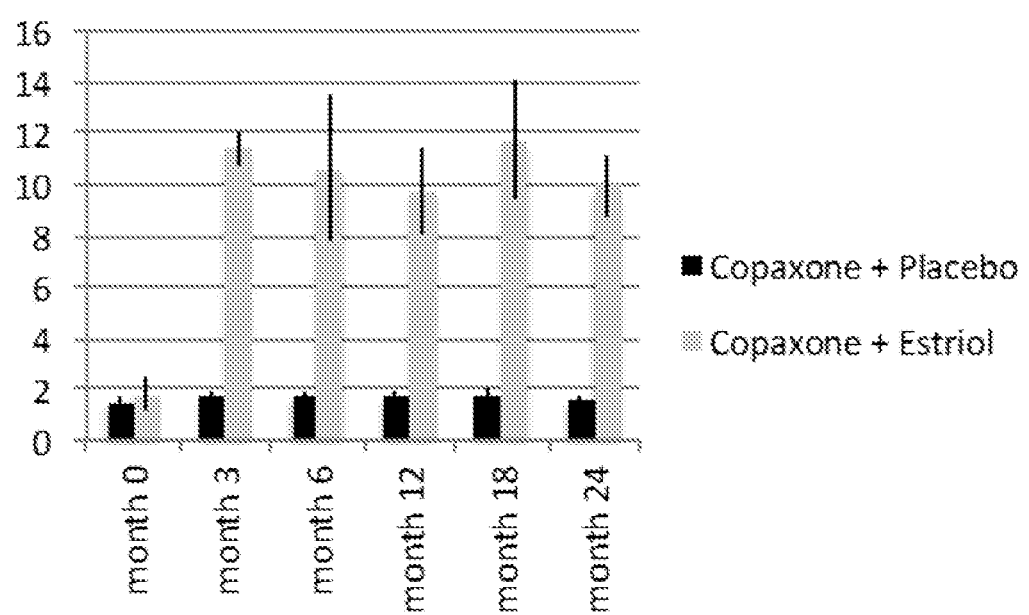
FIG. 6 is a bar graph depicting estriol blood levels induced by treatment with estriol 8 mg per day every day plus norethindrone 0.7 mg a day for 14 days every 3 months. Levels are expressed as ng/ml. Data for "month 0" represents pre-treatment baseline.

FIG. 6 depicts estriol blood levels induced by treatment with estriol 8 mg per day every day plus norethindrone 0.7 mg a day for 14 days every 3 months. Induced levels of about 10 ng/ml are comparable to the level typically observed in mid-pregnancy.

INCORPORATION BY REFERENCE

All patents, published patent applications, and other publications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

The invention claimed is:

1. A method of improving cognition in a subject with relapsing-remitting multiple sclerosis, comprising
   administering orally to a subject in need thereof, on a continuous basis for a treatment period of 84 consecutive days (12 weeks), 8 mg of estriol daily;
   administering orally to the subject, for 14 consecutive days (2 weeks) of the treatment period, 0.7 mg of norethindrone daily; and
   administering subcutaneously to the subject, on a continuous basis for the treatment period, 20 mg of glatiramer acetate daily,
   wherein
   the method comprises at least four consecutive treatment periods;
   before the at least four consecutive treatment periods, the subject's PASAT score is less than 55;
   after the at least four consecutive treatment periods, the subject's PASAT score is at least about 10% higher than the subject's PASAT score before the at least four consecutive treatment periods; and
   the subject is a woman.

2. The method of claim 1, further comprising an administration termination regimen following the at least four consecutive treatment periods, wherein the administration termination regimen comprises
   administering to the subject, for a first period of 1-3 weeks, about 4 mg of estriol;
   administering to the subject, for a second period of 1-3 weeks following the first period, about 2 mg of estriol; and,
   after the second period, terminating administration of estriol to the subject.

3. The method of claim 2, wherein the method further comprises terminating administration of the norethindrone to the subject during the first period of the administration termination regimen.

4. The method of claim 1, wherein after the at least four consecutive treatment periods, the subject's PASAT score is at least about 25% higher than the subject's PASAT score before the at least four consecutive treatment periods.

5. The method of claim 1, wherein the method comprises five consecutive treatment periods, six consecutive treatment periods, seven consecutive treatment periods, or eight consecutive treatment periods.

6. The method of claim 1, wherein the estrogen and the progestogen are formulated together.

7. The method of claim 1, wherein the subject has a uterus.

8. The method of claim 1, wherein the subject is a premenopausal female.

9. The method of claim 1, wherein the subject is a perimenopausal female.

10. The method of claim 1, wherein the subject is experiencing progression of the multiple sclerosis.

11. The method of claim 1, wherein the subject has progressive walking disability.

12. The method of claim 1, wherein the subject is a postmenopausal female.

* * * * *